(12) United States Patent
Huang et al.

(10) Patent No.: US 11,760,979 B2
(45) Date of Patent: Sep. 19, 2023

(54) ISOLATED LIVER CANCER STEM CELL AND METHOD FOR DRUG SCREENING THEREOF

(71) Applicant: LICENSE BIOTECHNOLOGY Co., Ltd., Taipei (TW)

(72) Inventors: Wen-Cheng Huang, Taipei (TW); Szu-Meng Wu, New Taipei (TW)

(73) Assignee: LICENSE BIOTECHNOLOGY Co., Ltd., Taipei (TW)

( * ) Notice: Subject to any disclaimer, the term of this patent is extended or adjusted under 35 U.S.C. 154(b) by 773 days.

(21) Appl. No.: 16/784,230

(22) Filed: Feb. 6, 2020

(65) Prior Publication Data
US 2021/0246430 A1  Aug. 12, 2021

(51) Int. Cl.
*C12N 5/095* (2010.01)
*A61K 31/44* (2006.01)
*A01K 67/027* (2006.01)

(52) U.S. Cl.
CPC ........ *C12N 5/0695* (2013.01); *A01K 67/0278* (2013.01); *A61K 31/44* (2013.01); *A01K 2207/15* (2013.01); *A01K 2227/105* (2013.01); *A01K 2267/0393* (2013.01)

(58) Field of Classification Search
None
See application file for complete search history.

(56) References Cited

PUBLICATIONS

Liu et al., Efficient Enrichment of Hepatic Cancer Stem-Like Cells from a Primary Rat HCC Model via a Density Gradient Centrifugation-Centered Method. PLOS One, 2012. 7(4): e35720, 14 pages.*
Chu et al., Celecoxib Suppresses Hepatoma Stemness and Progression by up-regulating PTEN. Oncotarget, 2013. 5(6): 1475-1490).*
Chan et al., Rapid Induction of Orthotopic Hepatocellular Carcinoma in Immune-Competent Rats by Non-Invasive Ultrasound-Guided Cells Implantation. BMC Gastroenterology, 2010. 10:83. 11 pages.*
Shi et al., The Effect of Hepatic Progenitor Cells on Experimental Hepatocellular Carcinoma in the Regenerating Liver, Scandinavian Journal of Gastroenterology, 2013. 49(1). 99-108.*

* cited by examiner

*Primary Examiner* — Allison M Fox
*Assistant Examiner* — Kimberly A Aron
(74) *Attorney, Agent, or Firm* — Hannah Tien

(57) ABSTRACT

An isolated rat liver cancer stem cell line which is named as TW-1 is provided. A method for drug screening by using the isolated rat liver cancer stem cell line is also provided.

13 Claims, 9 Drawing Sheets

4(A)

4(B)

5(A)

5(B)

5(C)

5(D)

*In Vitro* drug screening test

6(A)

6(B)

*In Vivo* drug screening test

6(C)

6(D)

7(A)

7(B)

ISOLATED LIVER CANCER STEM CELL AND METHOD FOR DRUG SCREENING THEREOF

FIELD OF THE INVENTION

The invention relates to a liver cancer stein cell line and the use thereof, particularly, to an isolated liver cancer stein cell line and a use for drug screening by using the isolated liver cancer stein cell line.

BACKGROUND OF THE INVENTION

Hepatocellular carcinoma (HCC) is one of the most common cancer which shows leading cause of cancer mortality in many countries, including Taiwan. Invasion and metastasis are the two most critical signs of cancer and usually are the main causes of death, especially in patients of hepatocellular carcinoma. The high rate of tumor recurrence, mainly due to the intrahepatic metastasis of cancer cells, is the main problem involved in the survival of patients with hepatocellular carcinoma after curative resection. However, to the mechanism for hepatic cancer metastasis and recurrence is still unclear.

Since the first prospective identification of cancer stein cells (CSCs) in solid cancers, the CSC theory has recurred as a research topic of interest. Like normal stein cells, cancer stein cells have the capacity to self-renew, can give rise to different posterity, and utilize common signaling pathways (Yamashita et al., 2013; Zhang et al., 2014; Galuppo et al., 2014; Pu et al., 2015). They differ from normal stein cells in that they have tumorigenic activity that enables them to form tumors when transplanted into animals (Yamashita et al., 2013). It assumes that solid cancers are organized with a small number of cancer stein cells driving tumor growth, repopulation and metastasis.

The invention is to use an isolated cancer stein cell lines to establish a pattern of rat hepatic cancer tumorigenesis and metastasis, and uses this model to screen the efficacy of anticancer drugs.

BRIEF SUMMARY OF THE INVENTION

The invention is an isolated rat liver cancer stem cell line which is named as TW-1 deposited under the DSMZ Accession No. DSM ACC3375.

The isolated rat liver cancer stein cell line highly expresses at least one drug resistance gene against an anticancer drug, wherein the at least one drug resistance gene is selected from the group consisting of Abca1, Abca12, Abcb1a, Abcb1b, Abcc3, Abcc4, Abcg1, Abcg313, Acyp1, Cyp20a1, Cyp2u1, Cyp3a9, Cyp4b1, Cyp51, Gsta1, Gsta2, Gsta3, Gsta4, Gsta5, Gstcd, Gstm1, Gstm2, Gstm4, Gsto1, Gstp1, Gstt2, Gstt3, Mgst1 and Mgst2.

The isolated rat liver cancer stein cell line expresses biomarkers of CD133, CK-19, GSTP1, CD44, EpCAM, CD90 and ALDH.

The invention provides an in vivo drug screening method, comprising the following steps: (a) providing an animal model, wherein the animal model is selected from an animal with immunodeficiency or an animal with complete immune system; (b) administering an isolated rat liver cancer stein cell line into the animal model; and (c) administering at least one anticancer drug to treat the animal model of (b) for evaluating the efficacy of the at least one anticancer drug in inhibition of a condition induced by the isolated rat liver cancer stein cell line in the animal model.

The invention provides an in vitro drug screening method, comprising the following steps: (a) providing an isolated rat liver cancer stein cell line; and (b) providing at least one anticancer drug to treat the isolated rat liver cancer stein cell line for evaluating the efficacy of the at least one anticancer drug in inhibiting growth, regrowth or metastasis of the isolated rat liver cancer stein cell line.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
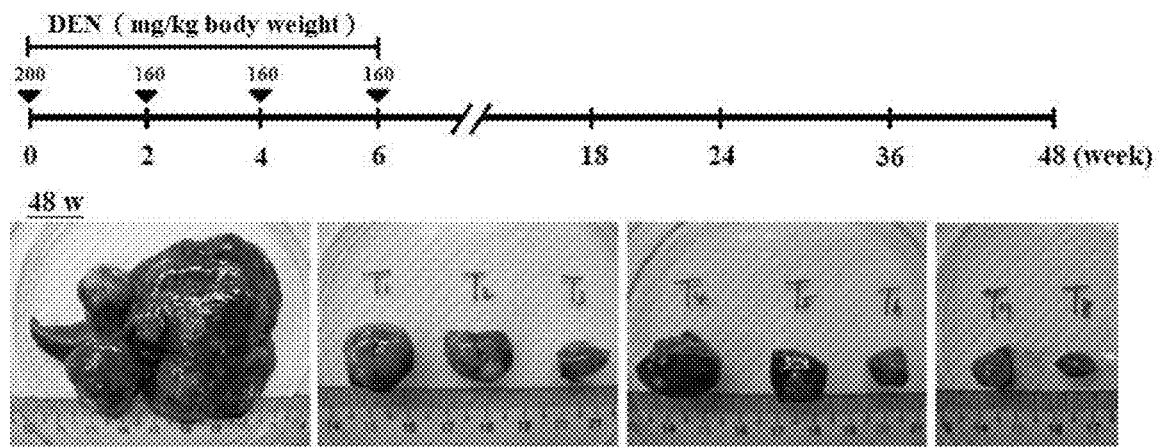
FIG. 1 shows processes and result of induction of liver cancer in Fisher 344 type rat.

An isolated rat liver cancer stein cell line which is named as TW-1 is provided in the invention, wherein the rat liver cancer stein cell line is isolated from a Fisher 344 type rat in which liver cancer is induced by diethylnitrosamine (DEN).

The isolated rat liver cancer stein cell line has been deposited in Food Industry Research and Development Institute in Taiwan.

The TW-1 cell line has been deposited under the Budapest Treaty at Leibniz Institute DSMZ-German Collection of Microorganisms and Cell Cultures (Inhoffenstr. 7B, D-38124 Braunschweig, German) on Mar. 23, 2023, and has been given the DSMZ Accession No. DSM ACC3375 by the International Depositary Authority. This biological material was subjected to the viability test on Apr. 4, 2023, and passed, and the deposit is capable of reproduction. The instant invention will be irrevocably and without restriction released to the public upon the issuance of a patent.

Particularly, the said anticancer drug is a hepatic cancer treating drug, preferably, the said hepatic cancer treating drug is Sorafenib.

One of the characterizations of the invention is that the isolated rat liver cancer stein cell line expresses biomarkers of CD133, CK-19, GSTP1, CD44, EpCAM, CD90 and ALDH.

The invention also provides an in vivo drug screening method which comprises the following steps: (a) providing an animal model, wherein the animal model is selected from an animal with immunodeficiency or an animal with complete immune system; (b) administering an isolated rat liver cancer stein cell line into the animal model; and (c) administering at least one anticancer drug to treat the animal model of (b) for evaluating the efficacy of the at least one anticancer drug in inhibition of a condition induced by the isolated rat liver cancer stein cell line in the animal model.

The animal model used in the in vivo drug screening method is Fisher 344 type rat or BALB/cAnN.CgFoxnl$^{nu}$/CrlNarl mouse.

In the in vivo drug screening method, wherein the isolated rat liver cancer stein cell line is administered into the animal model liver via orthotopic implantation, and the condition induced by the isolated rat liver cancer stein cell line is growth of tumor cell, recurrence of tumor cell or metastasis of tumor cell.

An in vitro drug screening method is also provided in the invention, in which the method comprises the following steps: (a) providing an isolated rat liver cancer stein cell line; and (b) providing at least one anticancer drug to treat the isolated rat liver cancer stein cell line for evaluating the efficacy of the at least one anticancer drug in inhibiting growth, regrowth or metastasis of the isolated rat liver cancer stein cell line.

The isolated rat liver cancer stein cell line used in the drug screening method is isolated from a Fisher 344 type rat in which liver cancer is induced by diethylnitrosamine (DEN), and the at least one anticancer drug used in the drug screening method is a hepatic cancer treating drug.

Examples

The examples below are non-limiting and are merely representative of various aspects and features of the present invention.

1. Induction, Isolation and Identification of Liver Cancer Cells

1a. Selection and Grouping of Animal Models

Wild Fisher 344 type male rats and BALB/cAnN.Cg-Foxnl$^{nu}$/CrlNarl male mice were selected as animal models in the experiment, all of those animals were bought from National Laboratory Animal Center of Taiwan. All the animas were kept in standard plastic cages, the ambient temperature was maintained at 25±2° C., and the light cycle was 12 hours. The animals were allowed free access to food and tap water ad libitum during the experiment.

The experimental animals were grouped into control group and experimental group, 6 rats or mice were delivered in each group.

1b. Induction of Liver Cancer in Fisher 344 Type Rat

Diethylnitrosamine (DEN) was chose and was prepared to working concentration with phosphate buffer solution (PBS) for inducing liver cancer in wild Fisher 344 type male rats.

As shown in FIG. 1, 8 experimental groups of Fisher 344 type male rats (T1 to T8) were administered with DEN by intraperitoneal injection, total 4 doses were administered, each dose was given in every two weeks. The doses were sequentially 200 mg/kg body weight, 160 mg/kg body weight, 160 mg/kg body weight, and 160 mg/kg body weight. After 4 doses administration, the rats were euthanized after keeping for 48 weeks, and liver tumor tissue was removed from each rat for transplanting into BALB/cAnN.Cg-Foxnl$^{nu}$/CrlNarl male nude mice to analyze the formation of liver tumor.

PBS was given instead of DEN in control group by intraperitoneal injection.

1c. Transplantation and Isolation of Liver Tumor Cells

Figure 2:
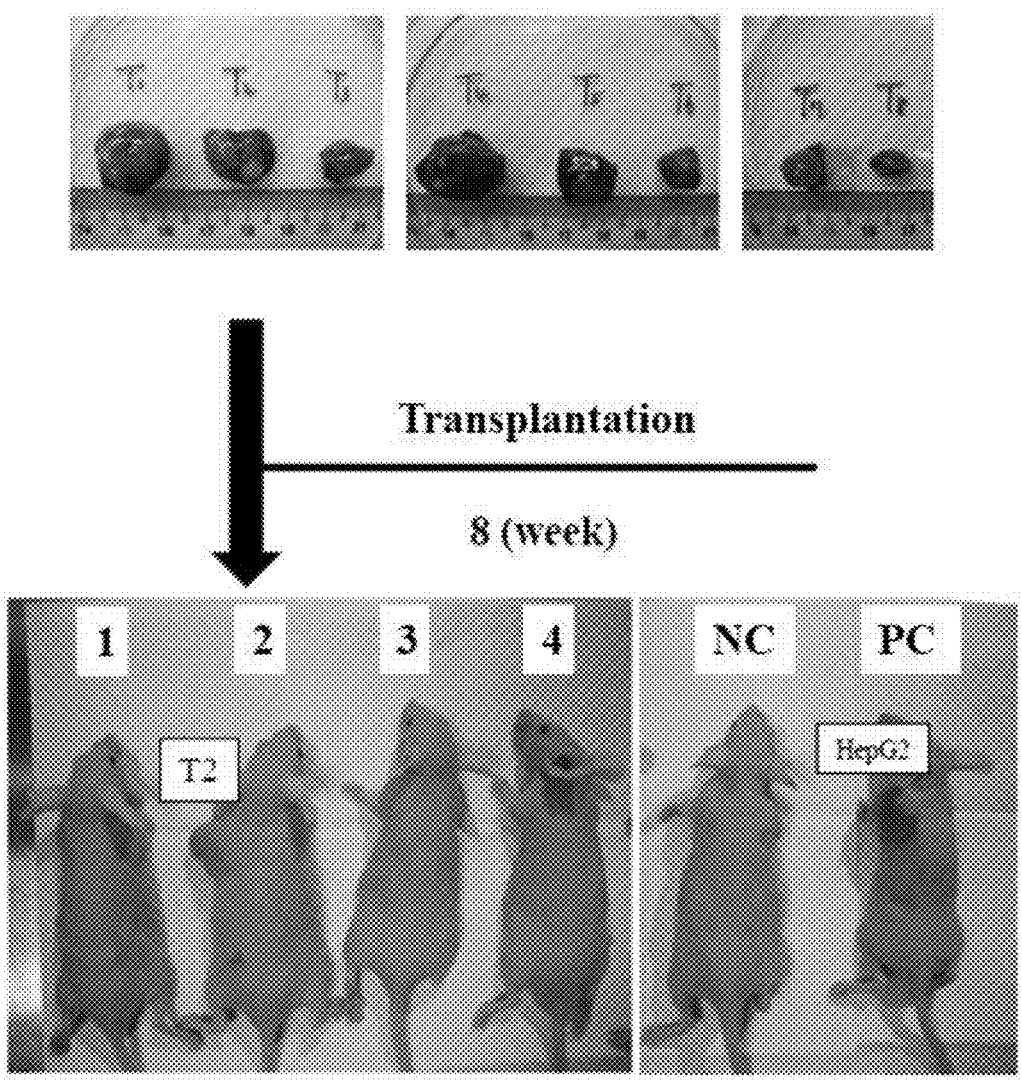
FIG. 2 shows gene microarray assay result of normal cells and the induced liver cancer cells.

As shown in FIG. 2, the liver tumor tissues of experimental rat were further processed into small pieces and were correspondingly transplanted into experimental group BALB/cAnN.CgFoxnl$^{nu}$/CrlNarl male nude mice (group NO.1 to NO.8) by subcutaneous embedding. The control groups mice were treated with transplantation of human liver cancer cell line HepG2 by subcutaneous injection (positive control group) and were administered with PBS by subcutaneous injection (negative control group). The tumor formation of all mice were observed for 8 weeks.

Figure 3:
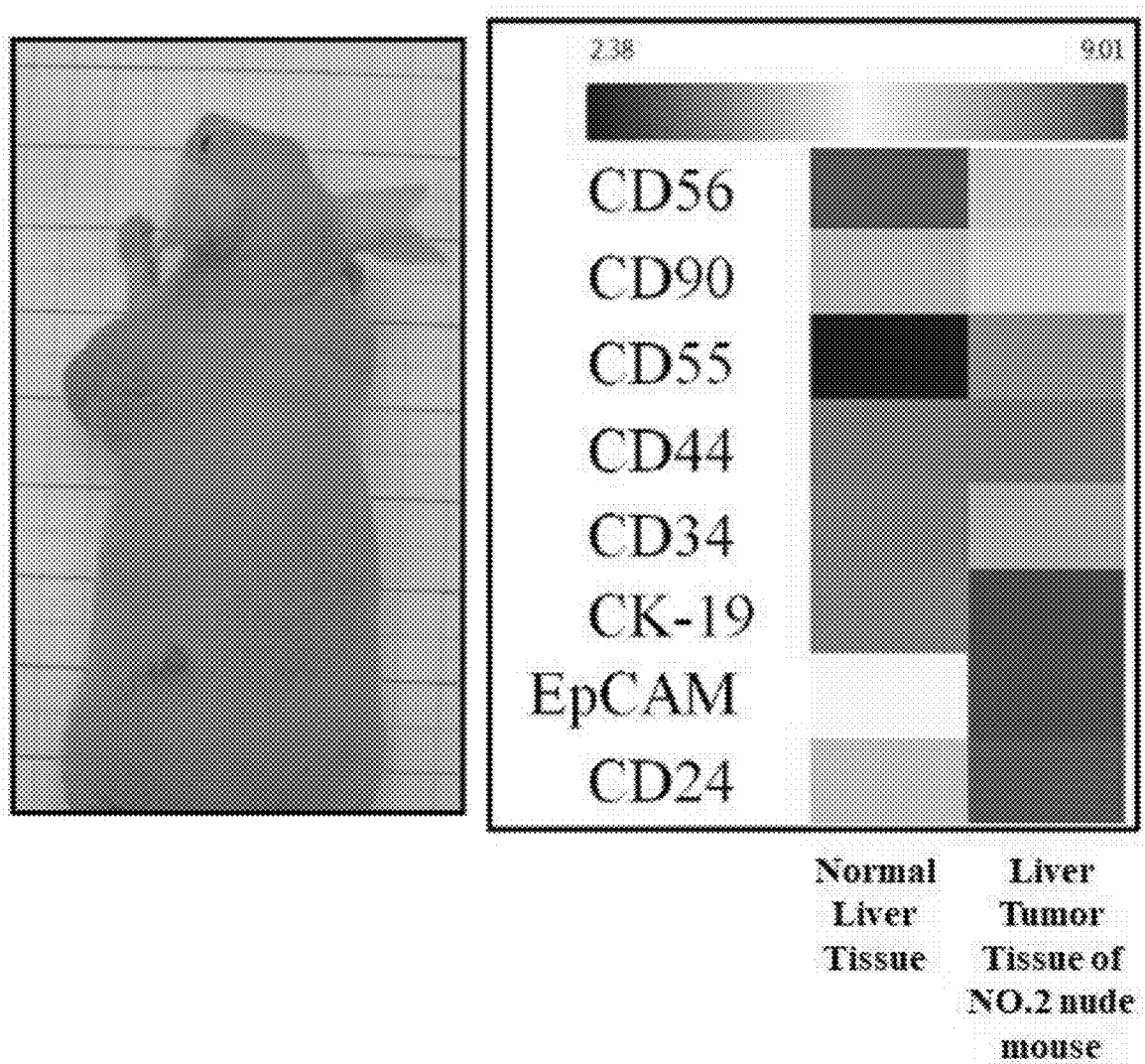
FIG. 3 shows processes of transplantation of liver cancer cells into BALB/cAnN.Cg-Foxnl$^{nu}$/CrlNarl mice.

The result showed that the liver tumor formation was most obvious in group NO.2 nude mouse that was transplanted liver tumor tissue of experimental rat T2. The group NO.2 nude mouse was euthanized and its liver tumor tissue was therefore analyzed by gene microarray. Normal liver tissue from control group mouse was used as control. As shown in FIG. 3, the liver tumor tissue of group NO.2 nude mouse highly expressed most hepatic oncogenes, such as EpCAM, CK-19/Krt19, or GSTP-1. However, interestingly, some stein cell related genes, such as CD133/Prom1, CD90 and CD44, were also observed in the liver tumor tissue of group NO.2 nude mouse.

Cell screening and isolation of liver tumor tissue in NO.2 BALB/cAnN.Cg-Foxnl$^{nu}$/CrlNarl nude mouse were further processed.

The procedures of cell screening and isolation of liver tumor tissue grown in BALB/cAnN.CgFoxnl$^{nu}$/CrlNarl mice is shown in FIG. 4(A).

The liver tumor tissue were processed into small pieces, 0.05% of collagenase was added for digestion for 1 hour in 37° C. incubator. The digested isolated cells were following cultured with DMEM/F12 media for 7 days, the attached live cells were sub-cultured by using 0.25% of trypsin-EDTA. Cells were collected respectfully depend on the time difference of cell suspension.

Repeating the process twice, several colonies of cell were observed under microscope, each colony was corrected. Two different cell lines were isolated by different cell morphologies, they are named TW-1 cell line and HTC cell line respectfully. The cell morphologies of TW-1 cell line and HTC cell line are shown in FIG. 4(B).

TW-1 cell line and HTC cell line were maintained in a modified DMEM/F12 medium (Invitrogen, Carlsbad, Calif.) supplemented with 10% fetal bovine serum (HyClone Laboratories, Logan, Utah), 80 units/ml penicillin, 80 μg/ml streptomycin, and 0.0175 mg/ml L-proline (Sigma).

1d. Identification of Cell Lines

Figure 5:
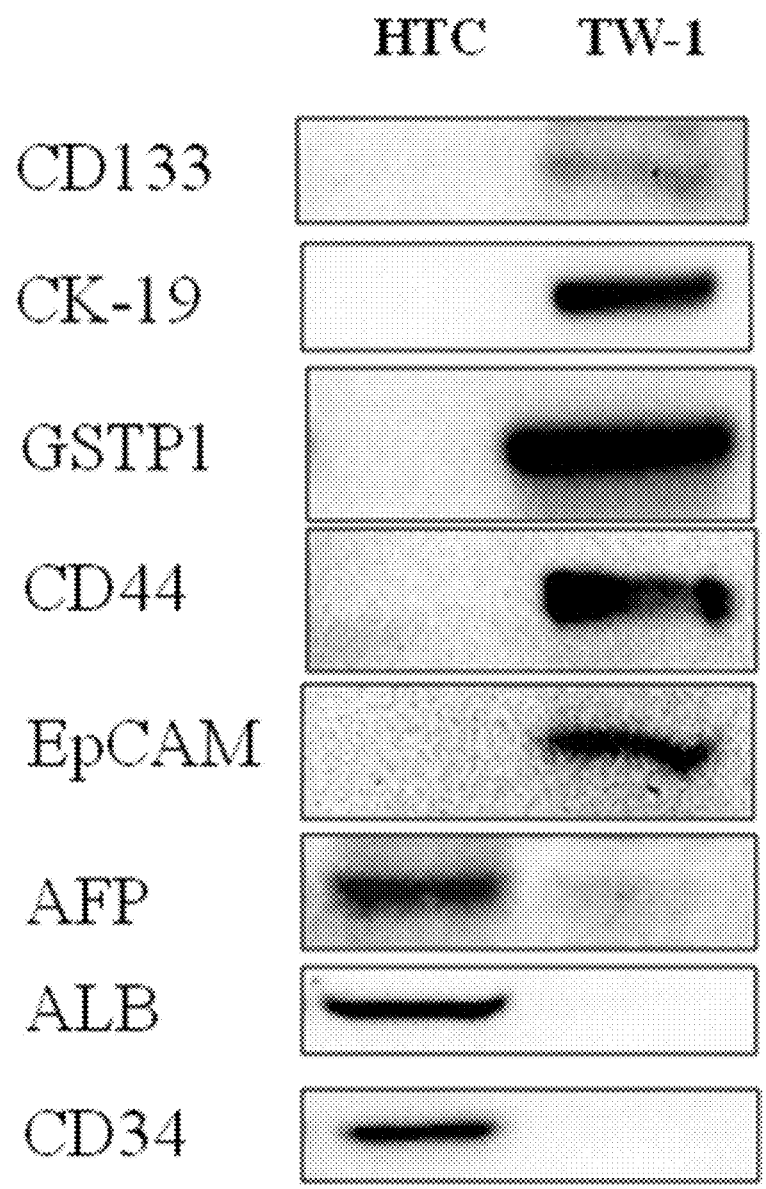
FIG. 5 shows the cell identification of the isolated tumor cell lines. 5(A) shows the result of western blot for identifying TW-1 cell line and HTCs; 5(B) shows the result of gene microarray assay result for identifying TW-1 cell line and HTCs; 5(C) shows processes of tumor regeneration test; 5(D) shows result of tumor regeneration test.
Figure 5:
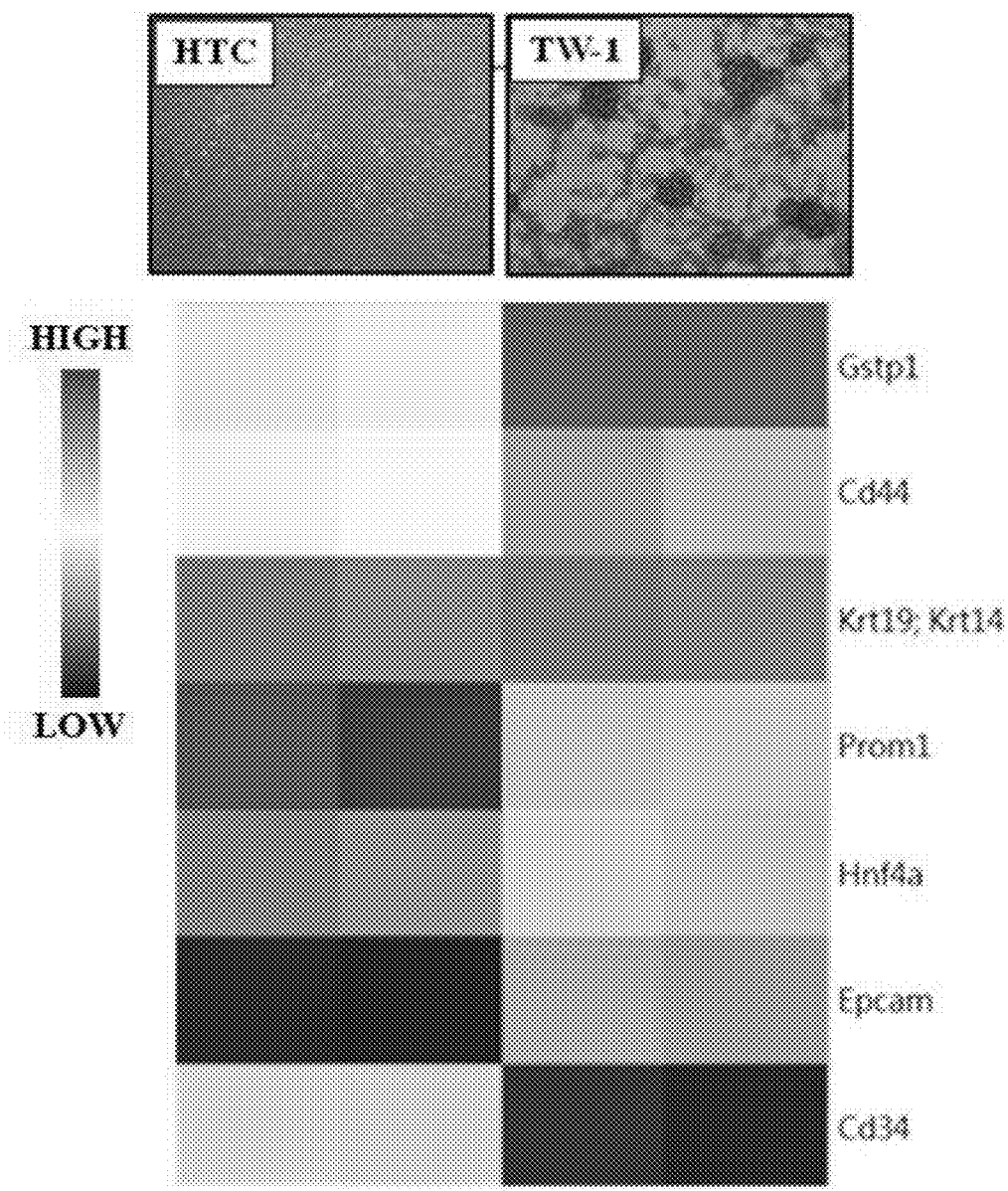
Figure 5:
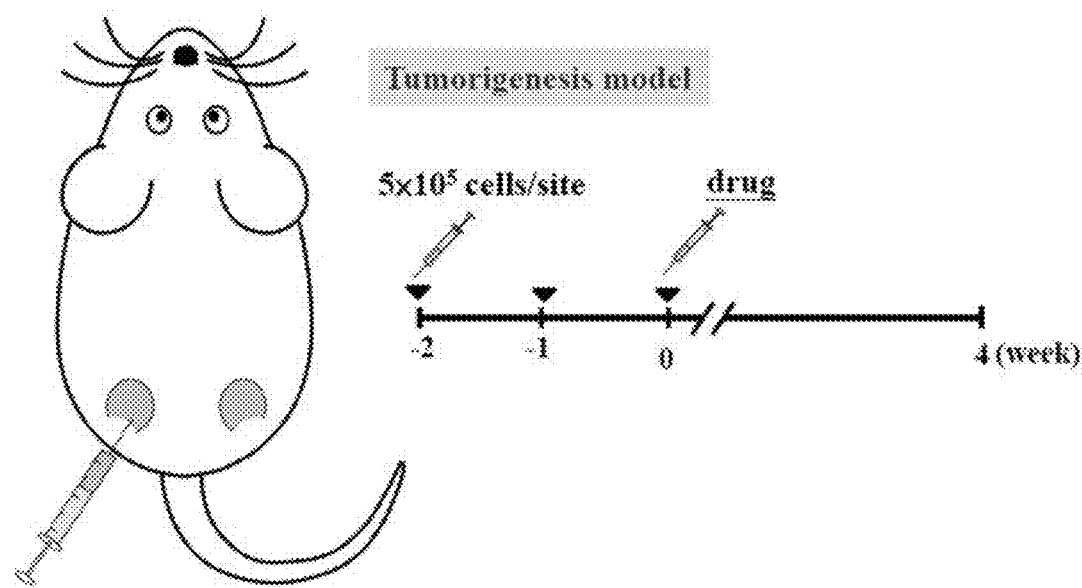
Figure 5:
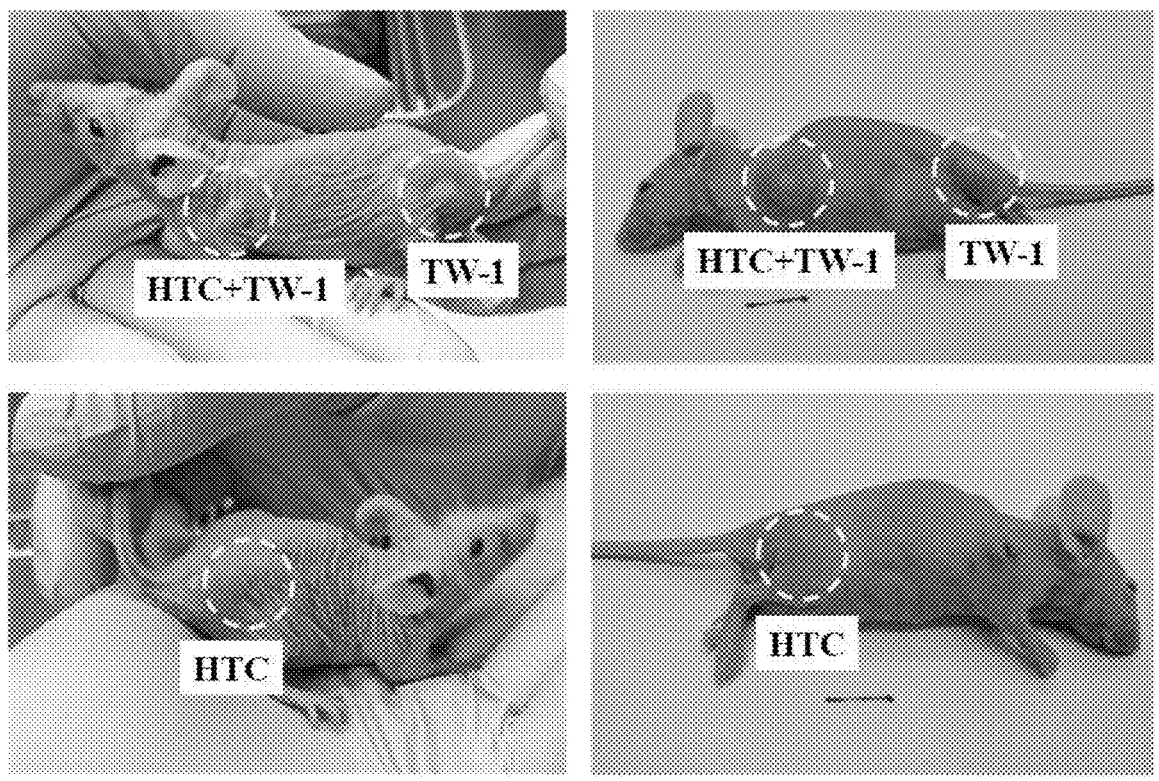

Western blot was performed for protein analysis of liver cancer or stein cell related biomarkers of TW-1 cell line and HTC cell line, including CD133, CK-19, GSTP-1, CD44 EpCAM, AFP, ALB and CD34. The result is shown in FIG. 5.

FIG. 5(A) indicates the difference between TW-1 cell line and HTC cell line. Comparing with HTC cell line, the stein cell related biomarkers CD133 and CD44 were highly expressed in TW-1 cell line, and TW-1 cell line also significant highly expressed liver cancer related biomarkers CK-19, GSTP-1 and EpCAM. In contrast, HTC cell line shows higher level of liver cancer biomarkers AFP and ALB than those in TW-1 cell line.

Further analyzing TW-1 cell line and HTC cell line by gene microarray, as shown in FIG. 5(B), some weakly expressed biomarker genes (such as CD44) shown in FIG. 2 were observed in TW-1 cell line, simultaneously, TW-1 cell line also expressed stein cell related genes Prom 1 (CD133), CD90 and so on. The above information preliminarily showed that the TW-1 cell line was a group of cells with stein cell characteristics in tumor tissue.

Tumor regeneration test was processed for identifying isolated TW-1 cell line and HTC cell line, as shown in FIG. 5(C), TW-1 cell line and HTC cell line were administered into immunodeficient BALB/cAnN.CgFoxnl$^{nu}$/CrlNarl mice with $5 \times 10^5$ cells and were observed 4 weeks to evaluate the tumor regeneration ability of TW-1 cell line and HTC cell line. FIG. 5(D) shows that tumor regeneration merely occurred in the mice administered with TW-1 cell line, the result indicated that TW-1 cell line had the ability of tumor regeneration.

Figure 4:
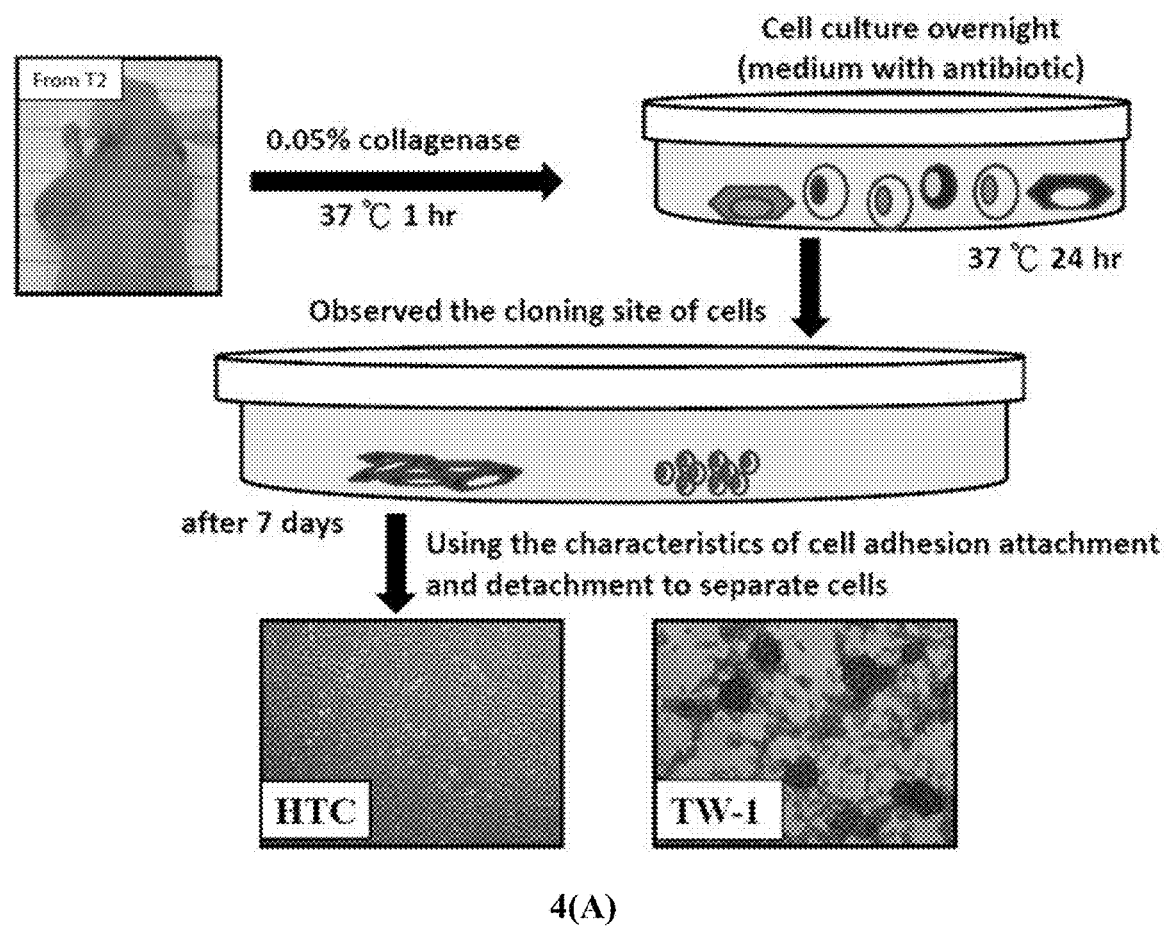
FIG. 4 shows selection and isolation of different cell lines from the induced liver cancer cells. 4(A) shows processes of the selection and isolation; 4(B) shows morphologies of the isolated cell lines, left one is named TW-1 cell line, right one is hepatic tumor cell lines (HTCs).
Figure 4:
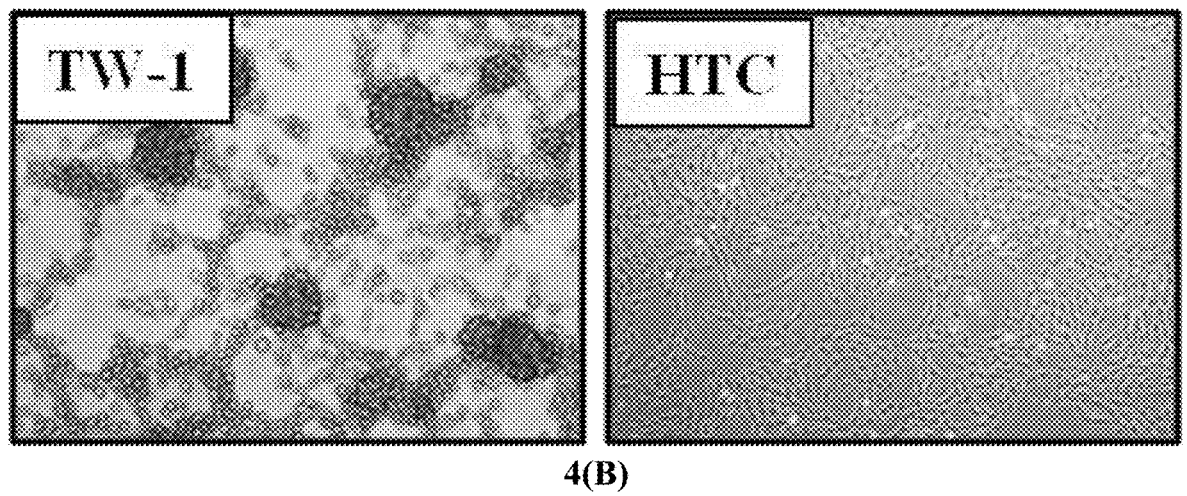

All the identification results as shown in FIG. 4 and FIG. 5 evidenced that TW-1 was a liver cancer stein cell line, and HTC cell line was a general liver cancer cell line.

The TW-1 cell line has been deposited under the Budapest Treaty at Leibniz Institute DSMZ-German Collection of Microorganisms and Cell Cultures (Inhoffenstr. 7B, D-38124 Braunschweig, German) on Mar. 23, 2023, and has been given the DSMZ Accession No. DSM ACC3375 by the International Depositary Authority. This biological material was subjected to the viability test on Apr. 4, 2023, and passed, and the deposit is capable of reproduction. The instant invention will be irrevocably and without restriction released to the public upon the issuance of a patent.

This deposit was made merely as a convenience for those of skill in the art and is not an admission that a deposit is required under 35 U.S.C. § 112.

2. Application of Method for Drug Screening

2a. In Vitro Drug Screening Test

The purpose of the method of drug screening is to evaluate the inhibitory ability of the active ingredients of currently used anticancer drugs against the growth, recurrence, or metastasis of TW-1 cell line, and HTC cell line was used as control group. The active ingredient of anticancer drug be used in the embodiment was Sorafenib.

TW-1 cell line and HTC cell line were seeded in 96-well plate with $2 \times 10^5$ cells/well, 1 μM, 5 μM, 10 μM, 20 μM and 40 μM of Sorafenib were respectfully used for treating cells once the cells were attached, and the negative control group cells were treated with PBS. The cell survival rate of cells was observed at 24 hours and 48 hours post-treatment.

Figure 6:
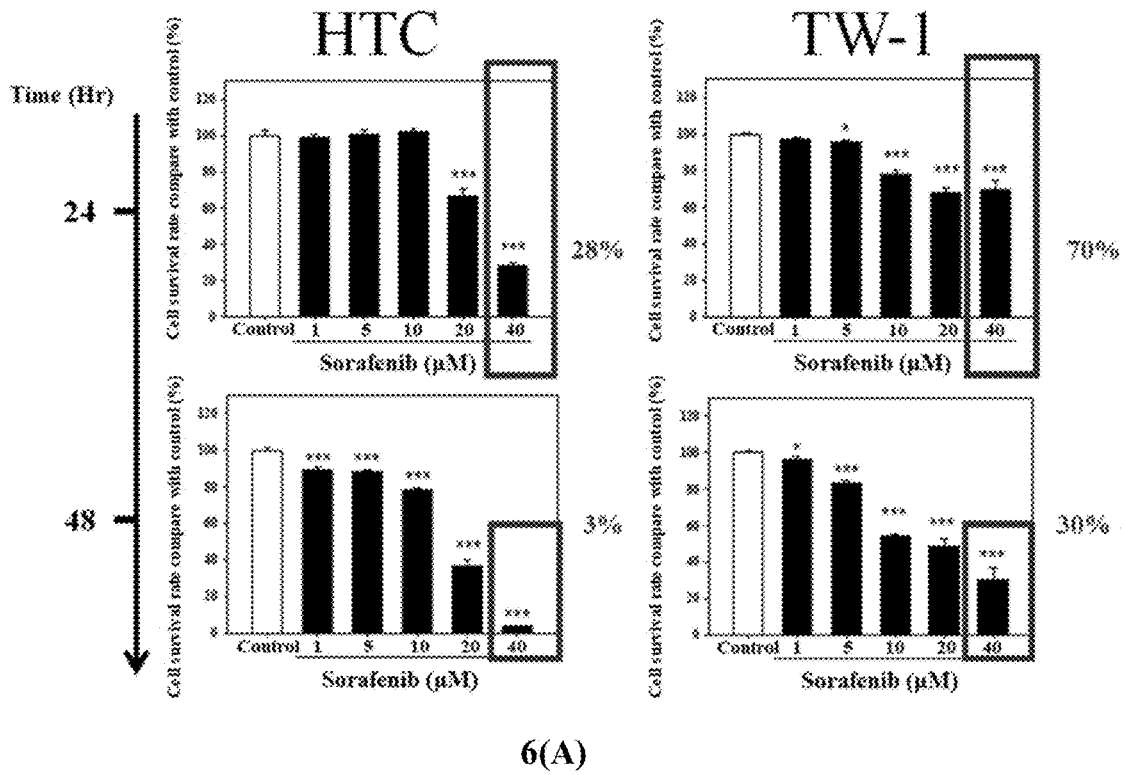
FIG. 6 shows results of drug screen test. 6(A) shows result of in vitro drug screen of Sorafenib; 6(B) shows gene microarray assay result of gene expression of drug resistance genes; 6(C) shows result of drug screen test of Sorafenib; 6(D) shows result of metastasis of TW-1 cell line post-treating with Sorafenib.
Figure 6:
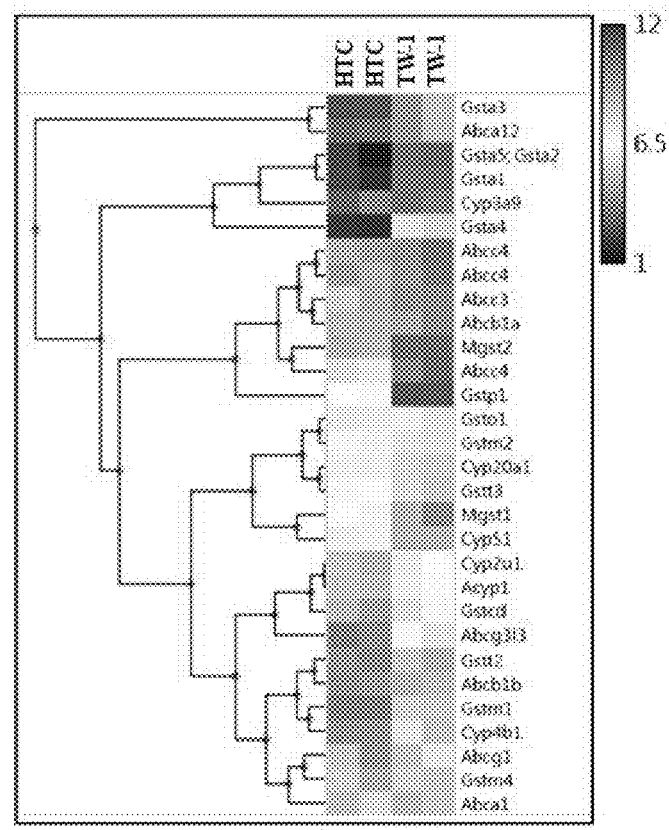
Figure 6:
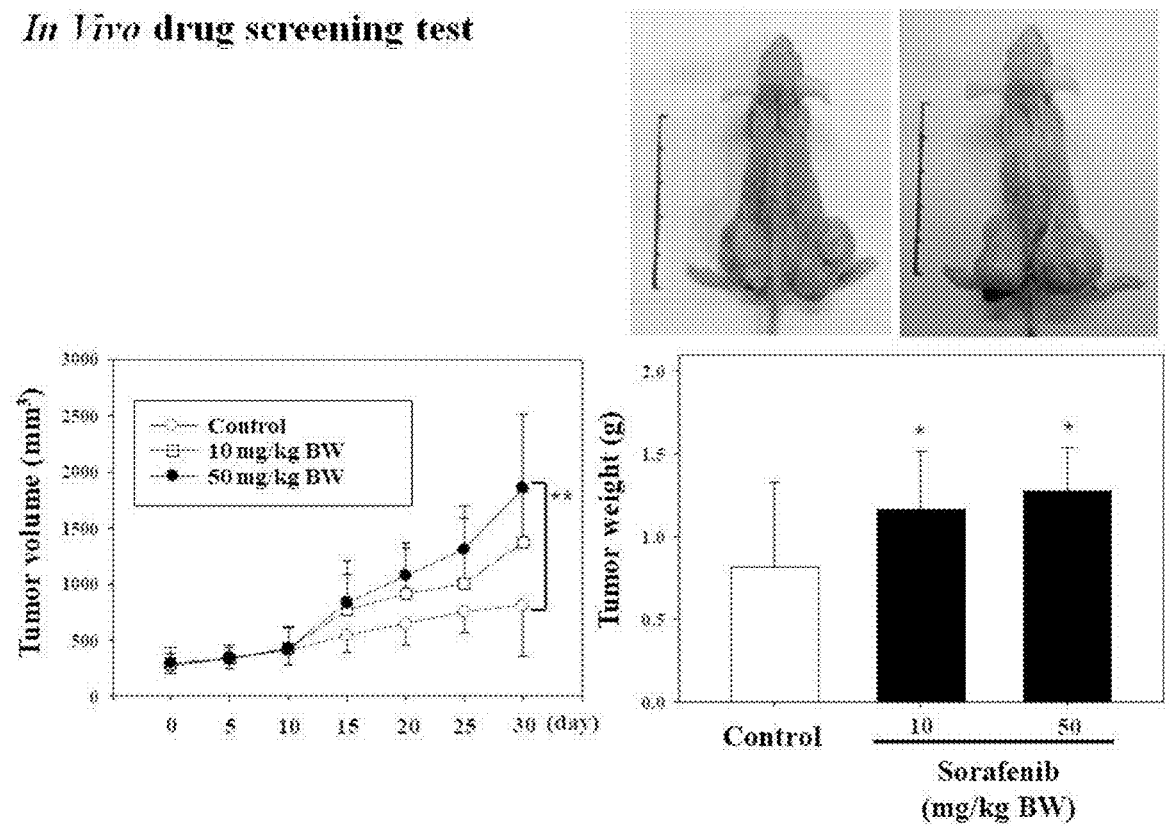
Figure 6:
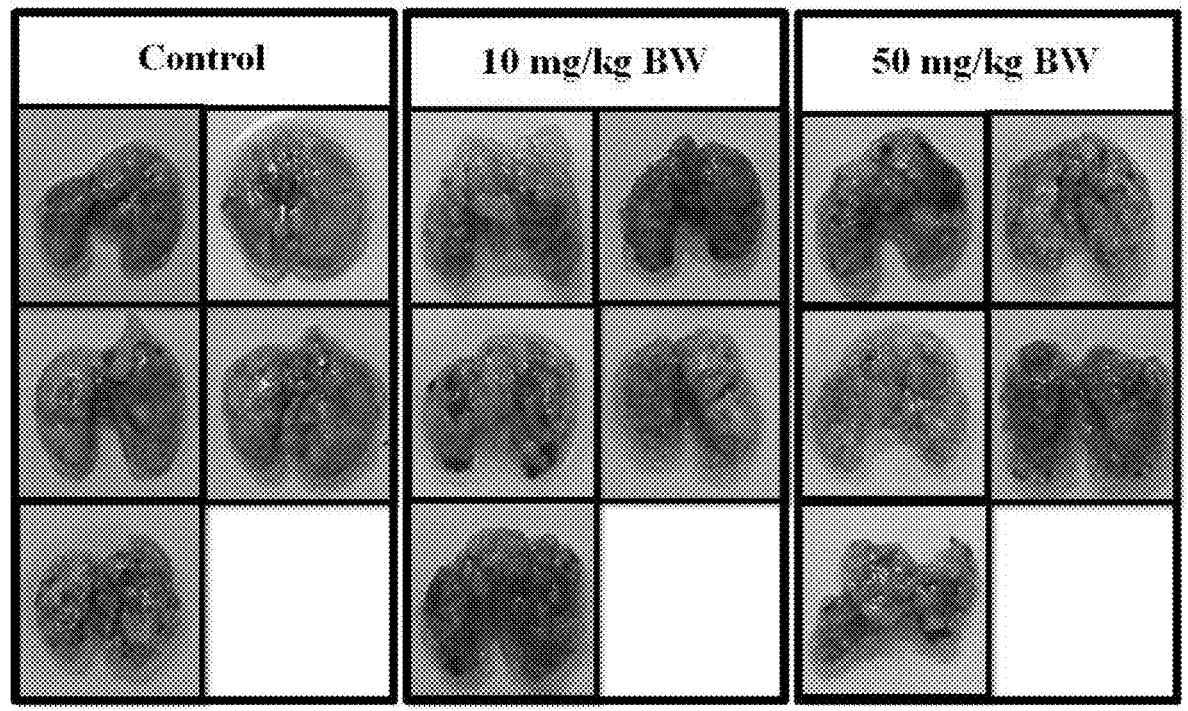

The result is shown in FIG. 6(A), TW-1 cell line showed higher sensitivity to Sorafenib with the concentration lower than 10 μM than the sensitivity to Sorafenib of HTC cell line after treatment for 24 hours. When increasing the concentration of Sorafenib to 40 μM, the cell growth was decreased. However, the result indicated that TW-1 cell line had much higher drug tolerance than it of HTC cell lines. This result was more obvious after 48 hours post-treatment.

To further investigate the reason of high drug tolerance of TW-1 cell line against high-dose Sorafenib, the gene microarray assays of TW-1 cell line and HTC cell line were processed. Comparison of the gene microarray results of TW-1 cell line and HTC cell line showed in FIG. 6(B), the drug resistance genes such as Abca1, Abca12, Abcb1 a, Abcb1b, Abcc3, Abcc4, Abcg1, Abcg313, Acyp1, Cyp20a1, Cyp2u1, Cyp3a9, Cyp4b1, Cyp51, Gsta1, Gsta2, Gsta3, Gsta4, Gsta5, Gstcd, Gstm1, Gstm2, Gstm4, Gsto1, Gstp1, Gstt2, Gstt3, Mgst1, Mgst2 etc. were highly expressed in TW-1 cell line rather than being expressed in HTC cell line. This result might explain that TW-1 cell line developed high drug resistance to high-dose Sorafenib through the effect of those drug resistance genes, which is one of the reasons that causes weak efficacy of drug treatment.

2b. In Vivo Drug Screening Test

The purpose of the method of drug screening is to evaluate the inhibitory ability of the active ingredients of currently used anticancer drugs against the growth, recurrence, or metastasis of TW-1 cell line, and BALB/cAnN.Cg-Foxnl$^{nu}$/CrlNarl nude mice were used as the animal model. The active ingredient of anticancer drug be used in the embodiment was Sorafenib.

BALB/cAnN.Cg-Foxnl$^{nu}$/CrlNarl nude mice were grouped into 3 groups, control group (Control), low-dose Sorafenib group (10 mg/kg body weight (BD)) and high-dose Sorafenib group (50 mg/kg body weight (BD)), 5 mice in each group.

Transplanting of TW-1 cell line into BALB/cAnN.Cg-Foxnl$^{nu}$/CrlNarl nude mice were processed with $5 \times 10^5$ cells by subcutaneous injection for evaluating the effect of anticancer drugs against TW-1 cell line.

After the tumor grew to appropriate size (100-150 mm$^3$) that was able to be measured at the TW-1 cell line transplanted position, the mice were treated with Sorafenib (Sorafenib groups) or PBS (control group) once per three days, and tumor generation of the mice were measured for 30 days the tumor volume of mice were recorded once per five days. As shown in FIG. 6(C), the tumor volume of all the groups were continuously increased. However, the tumor volume of Sorafenib treating groups were significantly higher than that in control group, surprisingly, the tumor volume of high-dose Sorafenib group mice were significantly higher than that in low-dose Sorafenib group mice.

According to the results shown in FIGS. 6(A) to 6(C), 40 μM Sorafenib had the ability to inhibit growth of TW-1 cell line, but TW-1 cell line was not killed. The gene microarray assay further indicated highly expressed drug resistance genes in TW-1 cell line. And the in vivo drug screen test indicated that the tumor volume of high-dose Sorafenib group mice were significantly higher than that in low-dose Sorafenib group mice. All the results evidenced that TW-1 cell line had drug resistance ability against Sorafenib, and all the results also explained why the recurrence and metastasis of liver cancer was so difficult to be controlled.

Moreover, as shown in FIG. 6(D), in vivo drug screen test also showed metastasis of TW-1 cell line to lung, and the metastasis was occurred drug dependent, high-dose Sorafenib induced high metastasis. The ability of immune evasion in TW-1 cell line was presumed.

3. Immune Evasion Test

3a. Selection and Pretreatment of Animal Models

Wild Fisher 344 type rats with complete immune system were selected as animal models.

30 mg/kg-body weight Retrorsine was administered by intraperitoneal injection once a week for two weeks to inhibit cell proliferation in liver for improving the growth advantage of TW-1 cell line in the intracellular microenvironment.

3b. Immune Evasion Test of Orthotopic Model

After treating Retrorsine for two weeks, and stopped administration for one week to metabolize the remaining Retrorsine, TW-1 cell line was further injected into liver of the rats with $2 \times 10^7$ cells, and the rats were kept for four weeks.

Figure 7:
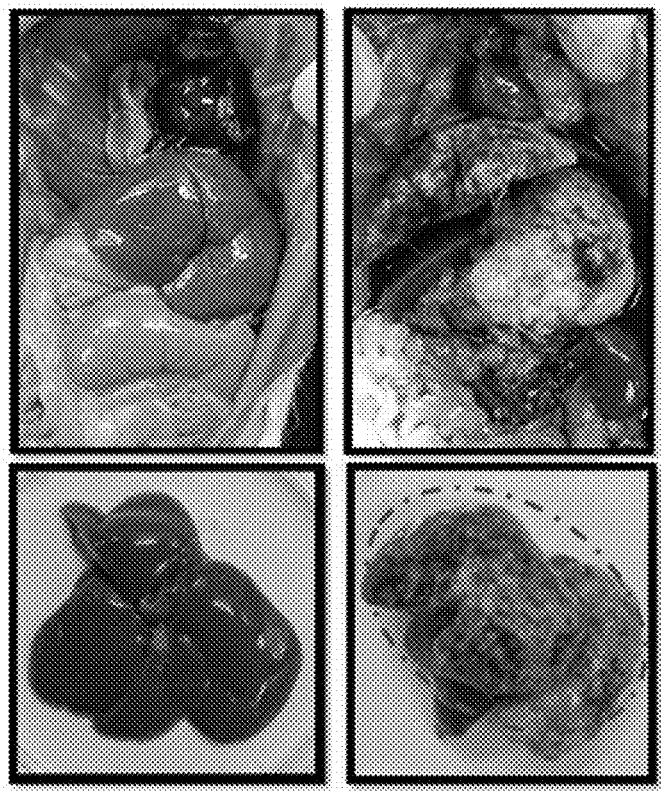
FIG. 7 shows processes and results of immune evasion test. 7(A) shows result of orthotopic model immune evasion test; 7(B) shows result of metastasis model immune evasion test.
Figure 7:
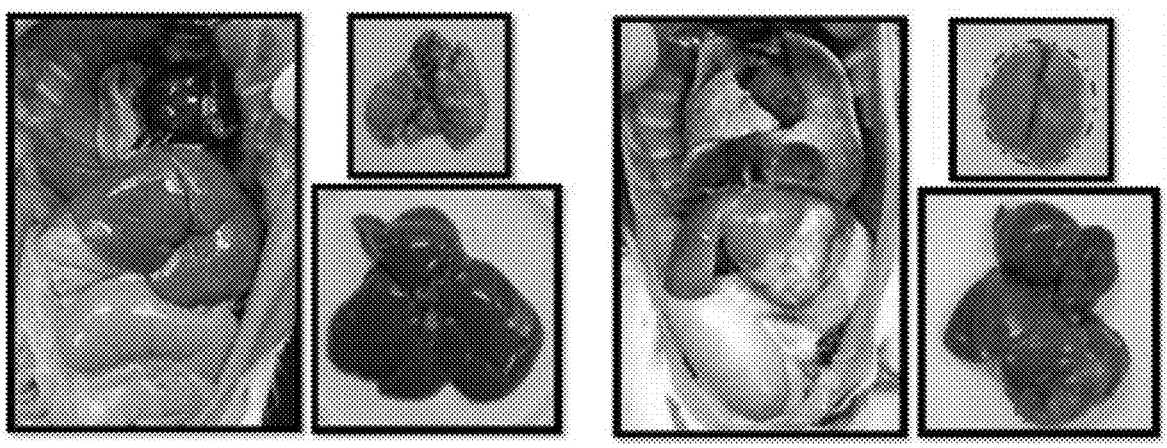

See FIG. 7(A), the result showed that a bunch of tumor cells occurred in the liver of orthotopic model rats, this result explained that TW-1 cell line had the ability to evade attack of immunocytes and to continuously proliferate.

3c. Immune Evasion Test of Metastasis Model

After treating Retrorsine for two weeks, and stopped administration for one week to metabolize the remaining Retrorsine, TW-1 cell line was further injected into liver of the rats with $2\times10^7$ cells, and the rats were kept for four weeks.

See FIG. 7(B), the result showed that a bunch of tumor cells did not only occur in the liver, but also metastasize to lung of metastasis model rats in four weeks, this result explained that TW-1 cell line did not only have the ability to evade attack of immunocytes and to continuously proliferate, but also metastasize to other organs around liver.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The cells, animals, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

What is claimed is:

1. An isolated rat liver cancer stem cell line which is named as TW-1 deposited under the DSMZ Accession No. DSM ACC3375, wherein the TW-1 has a drug resistance against Sorafenib.

2. The isolated rat liver cancer stem cell line according to claim 1, wherein the rat liver cancer stem cell line is isolated from a Fisher 344 type rat in which liver cancer is induced by diethylnitrosamine (DEN).

3. The isolated rat liver cancer stem cell line according to claim 1, wherein an expression level of at least one drug resistance gene against Sorafenib in the isolated rat liver cancer stem cell line is higher than a hepatic tumor cell line, wherein the at least one drug resistance gene is selected from the group consisting of Abca1, Abca12, Abcb1a, Abcb1b, Abcc3, Abcc4, Abcg1, Abcg313, Acyp1, Cyp20a1, Cyp2u1, Cyp3a9, Cyp4b1, Cyp51, Gsta1, Gsta2, Gsta3, Gsta4, Gsta5, Gstcd, Gstm1, Gstm2, Gstm4, Gsto1, Gstp1, Gstt2, Gstt3, Mgst1 and Mgst2.

4. The isolated rat liver cancer stem cell line according to claim 1, wherein the isolated rat liver cancer stem cell line expresses biomarkers of CD133, CK-19, GSTP1, CD44, EpCAM, CD90 and ALDH.

5. A drug screening method, comprising:
   (a) providing an animal model, wherein the animal model is selected from an animal with immunodeficiency or an animal with a complete immune system;
   (b) administering an isolated rat liver cancer stem cell line which is named as TW-1 deposited under the DSMZ Accession No. DSM ACC3375 into the animal model for tumorigenesis, wherein the TW-1 has a drug resistance against Sorafenib;
   (c) administering at least one anticancer drug to treat the tumor in the animal model of step (b) for evaluating the efficacy of the at least one anticancer drug in treatment of hepatic tumor growth; and
   (d) the at least one anticancer drug is evaluated to have efficacy in treatment of hepatic cancer if the TW-1 tumor growth is inhibited by the at least one anticancer drug.

6. The method according to claim 5, wherein the isolated rat liver cancer stem cell line is administered into the animal model liver via orthotopic implantation.

7. The method according to claim 5, wherein the animal model is a Fisher 344 type rat or a BALB/cAnN.Cg-Foxnl$^{nu}$/CrlNarl mouse.

8. The method according to claim 5, wherein the condition induced by the isolated rat liver cancer stem cell line is growth of a tumor cell, recurrence of a tumor cell or metastasis of a tumor cell.

9. The method according to claim 5, wherein the rat liver cancer stem cell line is isolated from a Fisher 344 type rat in which liver cancer is induced by diethylnitrosamine (DEN).

10. The method according to claim 5, wherein the at least one anticancer drug is at least one hepatic cancer treating drug.

11. A drug screening method, comprising:
    (a) providing an isolated rat liver cancer stem cell line which is named as TW-1 deposited under the DSMZ Accession No. DSM ACC3375, wherein the TW-1 has a drug resistance against Sorafenib;
    (b) providing at least one anticancer drug to treat the TW-1 cell line for evaluating the efficacy of the at least one anticancer drug in inhibiting the growth, regrowth or metastasis of the TW-1, and
    (c) the at least one anticancer drug is evaluated to have efficacy in treatment of hepatic cancer if the half maximal inhibitory concentration ($IC_{50}$) of the at least one anticancer drug is lower than 16.97 µM at 48 hours post-treatment.

12. The method according to claim 11, wherein the rat liver cancer stem cell line is isolated from a Fisher 344 type rat in which liver cancer is induced by diethylnitrosamine (DEN).

13. The method according to claim 11, wherein the at least one anticancer drug is at least one hepatic cancer treating drug.

* * * * *